United States Patent
Memarzadeh

(10) Patent No.: US 10,004,683 B2
(45) Date of Patent: Jun. 26, 2018

(54) ANTIMICROBIAL FORMULATIONS

(71) Applicant: Common Pharma, Inc., San Carlos, CA (US)

(72) Inventor: Bahram Memarzadeh, San Carlos, CA (US)

( * ) Notice: Subject to any disclaimer, the term of this patent is extended or adjusted under 35 U.S.C. 154(b) by 0 days. days.

(21) Appl. No.: 15/182,601

(22) Filed: Jun. 15, 2016

(65) Prior Publication Data

US 2016/0367576 A1 Dec. 22, 2016

Related U.S. Application Data

(60) Provisional application No. 62/181,202, filed on Jun. 18, 2015.

(51) Int. Cl.
*A61K 9/00* (2006.01)
*A61K 47/32* (2006.01)
*A61K 33/22* (2006.01)
*A61K 9/08* (2006.01)

(52) U.S. Cl.
CPC .............. *A61K 9/0014* (2013.01); *A61K 9/08* (2013.01); *A61K 33/22* (2013.01); *A61K 47/32* (2013.01)

(58) Field of Classification Search
None
See application file for complete search history.

(56) References Cited

U.S. PATENT DOCUMENTS

| | | |
|---|---|---|
| 6,420,425 B1 | 7/2002 | Melman |
| 7,914,803 B2 | 3/2011 | Chowhan |
| 8,722,123 B2 | 5/2014 | Doyle |
| 2006/0165803 A1 | 7/2006 | Palacin |
| 2012/0128622 A1 | 5/2012 | Berman |
| 2015/0025020 A1 | 1/2015 | Garrigue et al. |

FOREIGN PATENT DOCUMENTS

CN    105362289    3/2016

*Primary Examiner* — Jeffrey H Murray
(74) *Attorney, Agent, or Firm* — Owen J. Bates

(57) ABSTRACT

A pharmaceutical formulation is disclosed which includes an acrylic acid polymer and boric acid at a pH of less then about 5.0 and more than about 2.0.

7 Claims, No Drawings

ANTIMICROBIAL FORMULATIONS

CROSS-REFERENCE TO RELATED APPLICATIONS

This application claims the benefit of U.S. provisional application 62/181,302 filed on 18 Jun. 2015.

BACKGROUND

Field of the Invention

This invention relates to antimicrobial compositions and formulations that provide local anti-fungus, anti-viral and antibacterial, anti-gram-positive and gram negative, activity when infected human or animal skin, tissue, nail and hair is treated. The composition can also be used for vaginal and oral infections or diseases.

PRIOR ART SUMMARY

Currently, multiple formulations with a variety of active ingredients and vehicles are prescribed, approved, marketed and used for topical infections including impetigo, acne, onychomycosis (fungal infection of a toe nail), viral infections, hair fungal infections, athlete's foot (tinea pedis) and other conditions.

Jublia® is a newly approved nail topical solution with limited efficacy and is sold as a prescription medication. The primary ingredient in Jublia® is efinaconazole which is present in a concentration of 10%. Jublia® is expensive due to the high concentration of the efinaconazole. In addition, it has a limited efficacy of about a 20% complete cure rate.

KERYDIN® is another newly approved product which is from Anacor Corporation. It is a 5% solution of tavaborole. It also has a similar efficacy and cost to that of Jublia®.

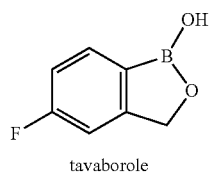 [SMILES: OB1OCc2cc(F)ccc21]

tavaborole

Medications for athlete's foot (tinea pedis) are mostly over-the-counter but severe cases are treated by the use of oral prescription medication. Examples of topical products are Lotrimin® which contains the drug clotrimazole in a 1% formulation and Lamisil®, a 1% terbinafine hydrochloride solution. The majority of marketed products are costly and not very effective or have side effects such as dry skin, rash and irritation

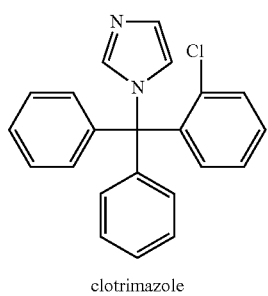

clotrimazole

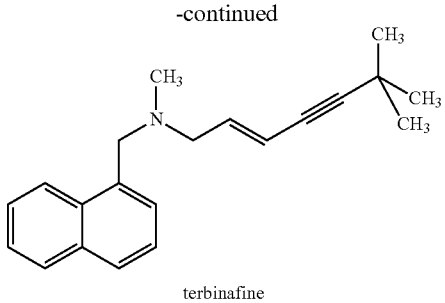

terbinafine

Summary of the Polymer Prior Art

An example of a simple formulation of a polycarbophil (an acrylic acid polymer) is shown below. This specific example shown below on the right is a linear, non-cross-linked polymer of acrylic acid.

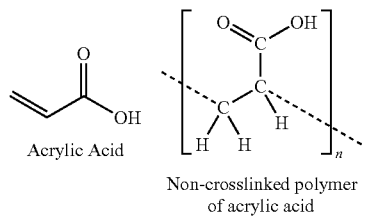

Noveon® AA-1 Polycarbophil

Noveon® AA-1 Polycarbophil, USP is a high molecular weight acrylic acid polymer crosslinked with divinyl glycol and is manufactured by Lubrizol Corporation of Wickliffe, Ohio. It provides excellent bioadhesive properties and has been used extensively to enhance the delivery of active ingredients to various mucous membranes. Noveon AA-1 Polycarbophil can be used for the formulation of buccal, nasal, ophthalmic, vaginal and rectal bioadhesive products. Noveon AA-1 Polycarbophil can also be used as a controlled release polymer in oral solid dose applications. Typical usage levels for achieving controlled release characteristics in tablets manufactured by aqueous granulation are 5-10 wt. %.

Noveon AA-1 and other cross-linked acrylic acid polymers are a line of pharmaceutical grade polymers. According to the manufacturer, Noveon AA-1 product line has a limited, acceptable pH range for proper gelling and stability. This pH range is between pH 5 and pH 8. More specifically, the recommended range is pH 6 to pH 7.

The standard procedure of gelling by neutralization, using chemical bases such as hydroxides or amines, is the only recommended method for formulating a polycarbophil that is described in the manufacturer's technical bulletins. To date, pharmaceutical and cosmetic preparations have not used these polymers at a pH below the lowest recommended pH. Neutralization procedures generally follow the recommendations made by the manufacturer to produce clinical, commercial and cosmetic products.

The current formulations for the treatment of topical microbial infections are largely dependent on such compounds as efinaconazole, tavaborole, clortrimazole and terbinafine. These are relatively complex organic compounds which are expensive to synthesize. There is a need for a topical formulation for the treatment of microbial infections which is based upon a relatively inexpensive non-organic active pharmaceutical ingredient.

SUMMARY OF THE PRESENT INVENTION

The current invention is based upon the use of boric acid and borate compounds in combination with a polymer which facilitates the application to topical sites and is relatively inexpensive. Boric acid and borate compounds have known anti-microbial characteristics but have never been used at a low pH with a polyacrylic polymer.

The primary effective ingredients of this composition are homo- and copolymers of acrylic acid polymers hydrated in water and added boric acid. The preferred polymers are cross-linked acrylic acid polymers that are marketed under the brand names such as Carbopol® and Noveon®-AA1. A polycarbophil is a generic drug used as a stool stabilizer. Chemically, it is a synthetic polymer of polyacrylic acid cross-linked with divinyl glycol or other cross-linking reagents. Carbopol® and Noveon® are trademarks of Lubrizol Advanced Materials, Inc. These polymers are referred to as polyacrylic acid or poly(acrylic acid). The most effective pH range of this formulation is about equal to or greater than 2 and about equal to or less than 5. The pH of the formulation can be achieved by the addition of small amounts of a dilute acid such as hydrochloric acid, acetic acid, ascorbic acid or citric acid. Most preferably the acid is 0.1N HCl.

In addition, boric acid has known anti-inflammatory properties. Such properties, in combination with anti-bacterial properties help in the effectiveness of the proposed composition in the treatment of Acne vulgaris.

The current invention is further distinguished by formulating the composition at a low pH (less than or equal to about pH 5.0) which is outside the normal range of use as recommended by the various manufacturers of the polyacrylic polymers.

The most effective pH range of this formulation is between about 2.0 and about 5.0 inclusive. The pH of the formulation can be lowered by the addition of small volumes of a dilute hydrochloric acid solution. This product is more effective at the low end of this pH range.

Formulation at this pH range requires a special method of preparation so that the gel formed by the polyacrylic polymer doesn't break, become clumpy and become non-homogeneous. Simple pH adjustment can result in the breaking of the polymer gel.

The solution to the problem is to add boric acid to a solution of the polymer which has not had its pH previously adjusted. This will result in a stable gel and the ability to adjust the pH to ~pH 3 (with a 1% boric acid and a 2% polymer concentration). All references to concentrations of any components of the various embodiments of the instant invention are references to percentage based on a W/W basis. A more accurate and desired pH can be achieved by adjusting the concentration of boric acid to a lower or higher concentration as needed to properly adjust the pH. Alternatively, a pH lower than 3.0 can be achieved by adding small amounts of dilute hydrochloric acid (for example HCl at 0.1N) until the desired pH is reached.

Formulating boric acid with a polycarbophil, especially at a pH of ≤5.0 is challenging since any addition of base (sodium borate or sodium hydroxide) will cause a dramatic reduction in viscosity (visible to the human eye) and a phenomena called the "crashing of the gel". It is also important to emphasize that the pH of boric acid solutions are just below pH 5. The pH of hydrated polycarbophil polymers, without any pH adjustment, is about 2.0. If the pH of a hydrated solution of the polyacrylic polymer is adjusted prior to the addition of boric acid, then sodium hydroxide or sodium borate would need to be added which runs the risk of crashing the gel or obtaining a pH outside of the accepted pH range.

The formulation and method of the present invention results in a boric-acid-containing gel-like formulation at a pH equal to or lower than about 5.0. Once applied on the skin, the formulation will dry in a short time (typically 5-10 minutes). The short drying time is far more convenient for the patient and enhances the retention of the formulation on the tissue and thus increases patient compliance and therapeutic effectiveness.

In one embodiment of the present invention, Noveon AA-1 was hydrated in distilled water by simple addition and mixing. Hydration can be determined by inspecting the solution. Full hydration was indicated by the optical uniformity of the solution. After full hydration, boric acid, in solution or as a powder, was added to achieve a concentration of borate from as little as about 0.5% up to about 5.5%. The solution was then mixed until the solution was visually clear. The pH was measured and was typically between 3 and 4 depending on the concentration of borate in the solution. The anti-microbial efficacies of boric and acrylic acid polymers are also enhanced by a lower pH.

The resulting gel was transferred into plastic or glass containers for use. The formulation was brushed or directly applied on a fungus infected nail (onychomycosis), skin or any infected area. The gel was then allowed to dry for 5 to 10 minutes. The treatment was repeated several times a day and for as many days as required. For example, if the formulation was used to treat onychomycosis, generally, the formulation will need to be applied for as long as it takes for an entire new nail to grow which is often 6-12 months.

In another example, the same process was used to produce the mixture but a pH adjustment step had been added. After the addition of boric acid, a low concentration borate buffer was added drop wise to adjust the pH to be above pH 3. The resulting gel was transferred into vials, tubes or other suitable storage devices for topical, dermal or ophthalmic treatment. The low concentration borate buffer was typically made up of a 1.0 mM solution of sodium borate with the pH adjusted with boric acid to a pH of about 8.0. The most important factor is that the $Na^+$ concentration of the low concentration borate buffer is at or below 0.1%. Other concentrations may be used as long as the $Na^+$ ion concentration is at or below 0.1%.

The present invention is based upon three new and non-obvious discoveries.

First: it is possible to formulate acrylic acid polymers with boric acid and obtain a consistent gel at a pH≤5.0 and a pH≥2.0.

Second: it is possible to formulate an effective gel with polyacrylic polymers and boric acid with stepwise pH adjustment using a sodium borate/boric acid buffer of very low concentrations.

Third: it is possible to formulate an effective gel by adjusting the pH of the mixture of polyacrylic polymers and boric acid in water to as low as 2.0 with the addition of dilute hydrochloric acid.

The present invention includes formulations composed of polyacrylic polymers and boric acid without pH adjustment resulting in a pH of about 3.2. The present invention also includes formulations of the same composition in which the pH was adjusted to a higher value by using diluted borate buffer solutions (sodium borate and boric acid) and having the pH adjusted upwards to a maximum of pH 5.0. Alternatively diluted hydrochloric acid could be used to adjust the pH of initial formulation (polyacrylic acid and boric acid) to as low as 2.0.

DETAILED DESCRIPTION

The present invention integrates the anti-microbial effectiveness of boric acid and the gel formation properties of a polyacrylic acid and its related cross-linked polymers in one, convenient, stable, safe, and effective formulation in which the pH is equal to or greater than about 2.0 and the pH is equal to or less than about 5.0. This formulation can also integrate additional pharmaceutically accepted excipients, polymers, fragrances, viscosity modifying agents, coloring substances, additional anti-microbial agents and antibiotics to have improved efficacy and/or patient compliance.

The present invention can be stored and utilized in a variety of containers, with or without brushes, delivery nozzles, applicators and performance containers such as atomizers, pumps, metered dosing or massaging tools. The viscosity of the formulation can be adjusted to be between 500 centipoises (cps) and 20,000 cps as needed in order to be compatible with the delivery or application device. The gel can be dispersed by an atomizer or metered dosing device since the gel is has sheer thinning properties and application of a mechanical delivery device will reduce the viscosity and enable it to be delivered from the container.

This disclosure describes a co-formulation of boric acid and polyacrylic acid polymers such as polycarbophil and specifically Noveon AA-1 and other members of the same family of polymers. The formulations are preferably produced only in water. However, a variety of emulsions and suspensions can be produced. Formulating boric acid in these polymers is done in manner that the resulting gel does not collapse or separate and retains some degree of stable viscosity. The addition of sodium hydroxide or high amounts of sodium borate will increase the pH and viscosity but will adversely affect the stability of the gel and eventually cause the collapse of the gel. This invention describes a method of pH adjustment, if needed, that does not result in such collapse of the gel and yields a therapeutically effective gel/borate formulation. This approach limits the presence of mono and divalent salts such as sodium or calcium which cause the collapse of the gel. In addition the pH must be adjusted to be equal or less than pH 5.0 and the pH is equal to or greater than 2.0.

PREFERRED EMBODIMENTS

I. One preferred embodiment has the following composition:
  boric acid 1%,
  Noveon AA-1 Polycarbophil 2%, and
  made up with purified water.
This results in a solution having a pH of about 3.13.
Procedure for Formulation:
  a. Noveon AA-1 (2 grams) was first hydrated in water (90 grams) for two hours at room temperature.
  b. Then 1 gram of boric acid which was suspended in 5 grams of water was added to the Noveon solution. The container that held the boric acid suspension was then rinsed with 2 grams of water which was also added to the Noveon AA-1 solution. As an alternative, the dry powered boric acid could be added directly to the Noveon AA-1 solution.
  c. This mixture was stirred for an additional 2 hours which yields the final formulation. This formulation resulted in a 1% boric acid and 2% Noveon AA-1 formulation. However the concentration for each can be in the range of 0.5% to 5.5%.

Depending on the ratio of the boric acid to the Noveon AA-1 the pH of the above solution can be acidic or basic.

II. If the pH of the solution above is too basic, it can be adjusted to be lower by the addition of a dilute HCl solution such as 0.1N HCl.

III. If the pH of the solution above is too acidic, it can be adjusted to be higher by the addition of a dilute borate solution such as 10 nM sodium borate.

IV. In another embodiment, an emulsion was made with a 20% acetone in water solution using a pharmaceutical grade of acetone and a surfactant, either non-ionic or ionic such as Poloxamer 188 (0.1 to 5%) or sodium dodecyl sulfate (0.1% to 1%). Poloxamers are nonionic triblock copolymers. Equal volumes of this emulsion and a 2x mixture of a polycarbophil polymer and boric acid in water (4% polycarbophil and 2% boric acid) were mixed to form a stable emulsion. This mixture can be applied on the tissue or nail and will dry faster due to the organic content.

In an alternative embodiment, any of the following solvents can be used in place of acetone:

TABLE I

| Pharmaceutically accepted solvents: (Class 3 of FDA listing) | |
|---|---|
| acetone | isobutyl acetate |
| acetic acid | isopropyl acetate |
| anisole | methyl acetate |
| 2-butanol | 3-methyl-1-butanol |
| 1-butanol | 2-methyl-1-propanol |
| butyl acetate | methylethyl ketone |
| tert-butylmethyl ether | methylisobutyl ketone |
| dimethyl sulfoxide | pentane |
| ethanol | propyl acetate |
| ethyl ether | 1-pentanol |
| ethyl acetate | 1-propanol |
| ethyl formate | 2-propanol |
| formic acid | |
| heptane | |

In an alternative embodiment, any of the following polyacrylic acid polymers shown in Table II can be used in place of Noveon AA-1.

TABLE II

| General Classes of Polyacrylic Acid Polymers Supplied by Lubrizol Corporation[1] |
|---|
| Carbopol ® homopolymers are polymers of acrylic acid crosslinked with allyl sucrose or allylpentaerythritol. |
| Carbopol ® copolymers are polymers of acrylic acid and C10-C30 alkyl acrylate crosslinked with allylpentaerythritol. |
| Carbopol ® interpolymers are carbomer homopolymers or copolymers that contain a block copolymer of polyethylene glycol and a long chain alkyl acid ester. |
| Pemulen ™ polymers are polymers of acrylic acid, modified by long chain (C10-C30) alkyl acrylates, and crosslinked with allylpentaerythritol |
| Noveon ® polycarbophil is a polymer of acrylic acid crosslinked with divinyl glycol. |

[1]The listed polymers are all of the same class as Noveon AA-1 but have different degrees of cross-linking and/or different cross-linkers. For the formulations disclosed herein, any of the above listed polymers can be substituted for Noveon AA-1. Adjustments in concentration may be needed to achieve the desired pH.

TABLE III

List of specific polymers offered by Lubrizol[2]

Carbopol® 934 NF Polymer
Carbopol® 934P NF Polymer
Carbopol® 940 NF Polymer
Carbopol® 941 NF Polymer
Carbopol® 1342 NF Polymer
Carbopol® 71G NF Polymer
Carbopol® 971P NF Polymer
Carbopol® 974P NF Polymer
Carbopol® 980 NF Polymer
Carbopol® 981 NF Polymer
Carbopol® ETD 2020 NF Polymer
Carbopol® Ultrez 10 NF Polymer
Pemulen™ TR-1 NF Polymer
Pemulen™ TR-2 NF Polymer
Noveon® AA-1 USP Polycarbophil

[2]Each of these specific polymers belong to one of the classes of polymers listed in Table II.

EXAMPLES

The following examples serve to further illustrate the present invention but are not meant in any way to limit or restrict the effective scope of the invention.

Example 1

300 grams of purified water was put in a glass bottle. Noveon AA-1, 2.2 gms, as a powder, was added gradually to the purified water and mixed to obtain full hydration of the polymer which takes about 2 hours. Separately, 3.3 gms of boric acid was added to 20 gms of purified water and mixed for 20 minutes to obtain a suspension. The boric acid suspension was added to the polymer mixture and mixed for one hour to fully dissolve the boric acid. The container holding the boric acid suspension was rinsed with 10 grams of purified water and added to the polymer mixture. Two additional aliquots of Noveon AA-1 (2.2 gms and 2.3 gms) were added to the mixture. Each aliquot was slowly added and mixed until full hydration (1 hour each). After full hydration of the second additional aliquot, the pH was 3.2 and it was not pH adjusted. Alternatively, the Noveon AA-1 could be added as a single aliquot.

Treatment Utilizing the Above Formulation

A formulation of the invention was applied to the left and right big toe of a patient having fungus infected toe nails. The formulation was placed in a small plastic bottle with a brush attached to the cap. The formulation was brushed on to fully coat the nail of the big toe and underneath the expose part of the nail and the nail bed. The exposed big toes were allowed to dry for 5-10 minutes. Then shoes and socks were put on and the patient went about normal daily activities. Application was repeated every morning from 12 Dec. 2014 to 20 Mar. 2015.

Measurements were made of the full length of each toe nail and the length of the healthy part of the nail. The ratio of healthy nail to total length of the nail is given below.

TABLE IV

Treatment of Toe Nail Fungus

|  | Left Toe | Right Toe |
|---|---|---|
| 12 Dec. 2014 | 0.18 (4 mm/22 mm) | 0.14 (3.2 mm/21 mm) |
| 29 Jan. 2015 | 0.33 (6 mm/18 mm) | 0.28 (5 mm/18 mm) |
| 27 Feb. 2015 | 0.40 (8 mm/20 mm) | 0.26 (5.5 mm/21 mm) |
| 20 Mar. 2015 | 0.50 (9 mm/18 mm) | 0.41 (7 mm/17 mm) |

As shown in Table IV, the ratio of healthy nail to full nail length increased almost 2.5 times during the dates recorded.

Example 2

20 grams of Noveon AA-1 was added to 970 grams of water and mixed/hydrated until all aggregates were cleared and hydrated (approximately 2 hours at low speed mixing with overhead mixer). 10 grams of boric acid was added directly to the hydrated polymer and mixed until dissolved, as opposed to the use of a suspension of boric acid in Example 1. Mixing continued for a total of one hour. An additional one hour of mixing was done in order to assure the uniformity of the mixture. The final pH was measured (results: 3.25). The resulting gel was filled into 15 mL glass, cobalt bottles with the brush/cap closure combination. Efficacy testing of this formulation is under way.

Example 3

The above formulation was used on a person with moderate acne vulgaris that had inflammatory and yellow-head lesions on the face. Most of the lesions were on the front of the face. In four days, 80% improvement was obtained and sustained with once per day application of the formulation with a small brush directly on the lesions.

Antimicrobial Effectiveness Testing

Sample 1

A formulation of a 1.5% borate with 2% Noveon was tested against 5 microorganisms:

a. *Aspergillus brasiliensis* (fungus)
b. *Candida albicans* (fungus)
c. *Escherichia coli* (bacteria)
d. *Pseudomonas aeruginosas* (bacteria)
e. *Staphylococcus aureas* (bacteria)

Testing was performed according to USP 38 <51>.

Test Sample

Log Reduction from Initial Inoculum

| Organism | 24 hours | 48 hours | 72 hours |
|---|---|---|---|
| a. *Aspergillus brasiliensis* (fungus) | 2.1 | 3.1 | 3.1 |
| b. *Candid albicans* (fungus) | 0.2 | 0.1 | 0.5 |
| c. *Escherichia coli* (bacteria) | 5.0 | 5.0 | 5.0 |
| d. *Pseudomonas aeruginosas* (bacteria) | 4.7 | 4.7 | 4.7 |
| e. *Staphylococcus aureas* (bacteria) | 5.0 | 5.0 | 5.0 |

Placebo

Log Reduction from Initial Inoculum

| Organism | 24 hours | 48 hours | 72 hours |
|---|---|---|---|
| a. *Aspergillus brasiliensis* (fungus) | 0.5 | 0.2 | 0.2 |
| b. *Candid albicans* (fungus) | 0.2 | 0.1 | 0.8 |
| c. *Escherichia coli* (bacteria) | 5.0 | 5.0 | 5.0 |
| d. *Pseudomonas aeruginosas* (bacteria) | 4.7 | 4.7 | 4.7 |
| e. *Staphylococcus aureas* (bacteria) | 5.0 | 5.0 | 5.0 |

Antimicrobial Effectiveness Testing

Sample 2

A formulation of a 1.5% borate with 2% Noveon was tested against 5 microorganisms:
  a. *Aspergillus brasiliensis* (fungus)
  b. *Candida albicans* (fungus)
  c. *Escherichia coli* (bacteria)
  d. *Pseudomonas aeruginosas* (bacteria)
  e. *Staphylococcus aureus* (bacteria)
Testing was performed according to USP 38 <51>.

Test Sample

Log Reduction from Initial Inoculum

| Organism | 14 days | 28 days |
|---|---|---|
| a. *Aspergillus brasiliensis* (fungus) | 4.6 | 4.6 |
| b. *Candid albicans* (fungus) | 4.1 | 4.1 |
| c. *Escherichia coli* (bacteria) | 5.0 | 5.0 |
| d. *Pseudomonas aeruginosas* (bacteria) | 5.0 | 5.0 |
| e. *Staphylococcus aureas* (bacteria) | 5.0 | 5.0 |

Placebo

Log Reduction from Initial Inoculum

| Organism | 14 days | 28 days |
|---|---|---|
| a. *Aspergillus brasiliensis* (fungus) | 0.1 | 0.9 |
| b. *Candid albicans* (fungus) | 3.0 | 3.5 |
| c. *Escherichia coli* (bacteria) | 5.0 | 5.0 |
| d. *Pseudomonas aeruginosas* (bacteria) | 5.0 | 5.0 |
| e. *Staphylococcus aureas* (bacteria) | 5.0 | 5.0 |

Dermal Irritation Test in New Zealand White Rabbits

The test was performed according to ISO 10993-10:2010. The test sample was 2% Noveon and 2% boric acid in water. A placebo was also tested which was only 2% Noveon in water. All testing was under GLP conditions. A negative control was used which was 0.9% Sodium Chloride for Injection, USP and a positive control was used which was 20% W/V of sodium dodecyl sulfate (SDS) in water.

The test animals were inspected at times 1, 24, 48 and 72 hours. All animals in the test, placebo and negative control groups showed no irritation at all. The positive control showed observational rankings of 2-4 with the rankings assigned as follows:

| Mean Score | Response Category |
|---|---|
| 0 to 0.4 | Negligible |
| 0.5 to 1.9 | Slight |
| 2 to 4.9 | Moderate |
| 5 to 8 | Severe |

Analytical Report

The test sample was analyzed and showed a pH of 3.0 and a viscosity of 6,000 cps when measured at 25° C. RVT, Spindle 27 at 20 rpm. The placebo was analyzed which showed a pH of 3.2 and a viscosity of 11,625 cps when measured at 25° C. RVT, Spindle 27 at 20 rpm.

Although the present invention has been described with reference to specific examples, it should be understood that various modifications and variations can be made by a person having ordinary skill in the art without departing from the spirit and scope of the invention. Accordingly, the above disclosure should be interpreted as illustrative only and should not to be interpreted in a limiting sense. The present invention is limited only by the scope of the following claims.

The invention claimed is:

1. A pharmaceutical formulation comprising:
   an aqueous solution of
     boric acid and
     one or more crosslinked acrylic acid polymers
   which has a pH lower than about 5.0.

2. A pharmaceutical formulation as described in claim 1 wherein the pH is lower than about 5.0 and the pH is higher than about 2.0.

3. A pharmaceutical formulation as described in claim 1 wherein the crosslinked acrylic acid polymer is selected from the group consisting of
   a homopolymer of acrylic acid crosslinked with allyl sucrose;
   a homopolymer of acrylic acid crosslinked with allyl pentaerythritol;
   a copolymer of acrylic acid and C10-C30 alkyl acrylate crosslinked with ally pentaerythritol;
   a polymer of acrylic acid modified by long chain C10-C30 alkyl acrylates and crosslinked with allyl-pentaerythirtol; and
   a polymer of acrylic acid crosslinked with divinyl glycol.

4. A pharmaceutical formulation as described in claim 3 wherein the crosslinked acrylic acid polymer is a polymer of acrylic acid crosslinked with divinyl glycol.

5. A pharmaceutical formulations as described in claim 1 wherein the boric acid is present at a concentration of about 0.5% to about 5.5%.

6. A pharmaceutical formulation as described in claim 1 wherein the crosslinked acrylic acid polymer is present in a concentration of less than about 5.5%.

7. A pharmaceutical formulation as described in claim 1 wherein the formulation has a viscosity of about 500 centipoises to about 20,000 centipoises.

* * * * *